(12) United States Patent
Riederer et al.

(10) Patent No.: US 6,201,986 B1
(45) Date of Patent: Mar. 13, 2001

(54) SYNCHRONIZED K-SPACE SAMPLING IN MAGNETIC RESONANCE ANGIOGRAPHY

(75) Inventors: Stephen J. Riederer; Sean B. Fain, both of Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 09/198,842

(22) Filed: Nov. 24, 1998

(51) Int. Cl.[7] ....................................................... A61B 5/55
(52) U.S. Cl. ............................ 600/419; 324/309; 324/306
(58) Field of Search .................................. 600/410, 411, 600/420; 324/307, 309

(56) References Cited

U.S. PATENT DOCUMENTS

| | | | |
|---|---|---|---|
| 5,604,435 | * | 2/1997 | Foo et al. ............................... 324/309 |
| 5,799,649 | * | 9/1998 | Prince .................................... 600/420 |
| 5,924,987 | * | 7/1999 | Meaney et al. ....................... 600/420 |

* cited by examiner

Primary Examiner—Brian L. Casler
(74) Attorney, Agent, or Firm—Quarles & Brady LLP

(57) ABSTRACT

A dynamic MRA study of a subject is performed using a 3D fast gradient-recalled echo pulse sequence after the subject is injected with a contrast agent. The sampling of k-space is synchronized with the peak of the contrast enhancement profile by sampling in an inward spiral pattern during the rise in enhancement and by sampling in an outward spiral pattern after peak enhancement occurs.

8 Claims, 6 Drawing Sheets

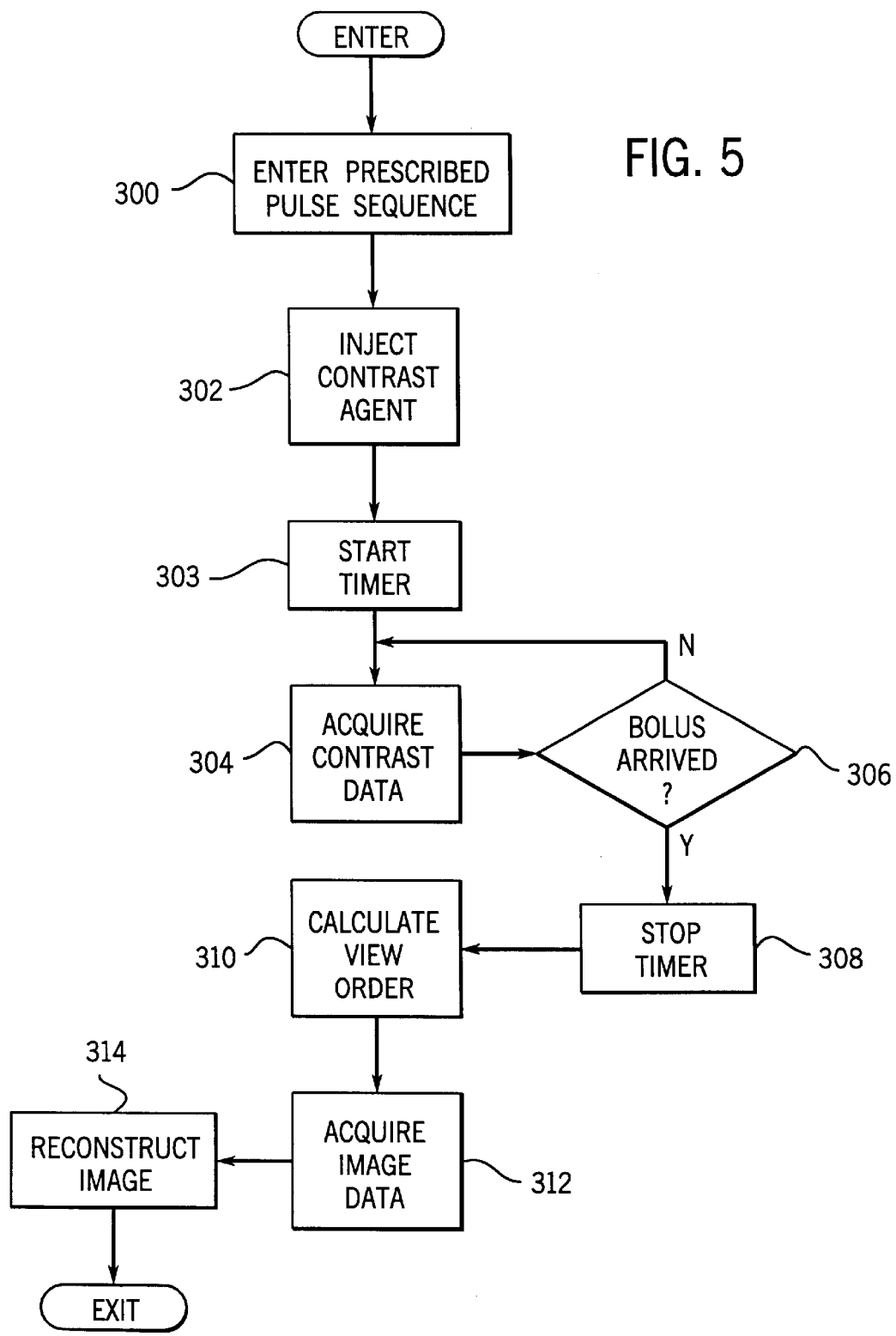

SYNCHRONIZED K-SPACE SAMPLING IN MAGNETIC RESONANCE ANGIOGRAPHY

BACKGROUND OF THE INVENTION

The field of the invention is magnetic resonance angiography ("MRA"), and particularly, dynamic studies of the human vasculature using contrast agents which enhance the NMR signals.

Diagnostic studies of the human vasculature have many medical applications. X-ray imaging methods such as digital subtraction angiography ("DSA") have found wide use in the visualization of the cardiovascular system, including the heart and associated blood vessels. Images showing the circulation of blood in the arteries and veins of the kidneys and the carotid arteries and veins of the neck and head have immense diagnostic utility. Unfortunately, however, these x-ray methods subject the patient to potentially harmful ionizing radiation and often require the use of an invasive catheter to inject a contrast agent into the vasculature to be imaged.

Magnetic resonance angiography (MRA) uses the nuclear magnetic resonance (NMR) phenomenon to produce images of the human vasculature. When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins, and after the excitation signal $B_1$ is terminated, this signal may be received and processed to form an image.

When utilizing these signals to produce images, magnetic field gradients ($G_x$ $G_y$ and $G_z$) are employed. Typically, the region to be imaged is scanned by a sequence of measurement cycles in which these gradients vary according to the particular localization method being used. Each measurement is referred to in the art as a "view" and the number of views determines the resolution of the image. The resulting set of received NMR signals, or views, are digitized and processed to reconstruct the image using one of many well known reconstruction techniques. The total scan time is determined in part by the number of measurement cycles, or views, that are acquired for an image, and therefore, scan time can be reduced at the expense of image resolution by reducing the number of acquired views.

MR angiography (MRA) has been an active area of research. Two basic techniques have been proposed and evaluated. The first class, time-of-flight (TOF) techniques, consists of methods which use the motion of the blood relative to the surrounding tissue. The most common approach is to exploit the differences in signal saturation that exist between flowing blood and stationary tissue. The improvement in blood-tissue contrast is due to the stationary tissues experiencing many excitation pulses and becoming saturated. Flowing blood, which is moving through the excited section, is continually refreshed by spins experiencing fewer excitation pulses and is, therefore, less saturated. The result is the desired image contrast between the high-signal blood and the low-signal stationary tissues.

To enhance the diagnostic capability of MRA a contrast agent such as gadolinium can be injected into the patient prior to the MRA scan. As described in U.S. Pat. No. 5,417,213 the trick is to acquire the central k-space views at the moment the bolus of contrast agent is flowing through the vasculature of interest. This is not an easy timing to achieve as part of a routine clinical procedure because the delay time between intravenous injection to arrival in the arterial vasculature of interest is highly patient-dependent. Therefore, some means is required for determining this delay time and synchronizing MR data acquisition to the contrast bolus profile. Such synchronization is necessary to provide adequate vessel contrast and to prevent artifacts such as edge enhancement of the vessel. Various means have been developed to provide accurate timing including: use of a small test injection of contrast as described by J. K. Kim, R. I. Farb, and G. A. Wright, *Test Bolus Examination in the Carotid Artery at Dynamic Gadolinium-enhanced MR Angiography*, Radiology, 1998, 206:283–289; real-time line scanning described by T. K. Foo, S. Manojkumar, M. R. Prince, and T. L. Chenevert, *Automated Detection of Bolus Arrival and Initiation of Data Acquisition in Fast, Three-dimensional, Gadolinium-enhanced MR Angiography*, Radiology 1997, 205:137–146; and real-time fluoroscopic imaging as described by A. H. Wilman, S. J. Riederer, B. R. King, J. P. Debbins, P. J. Rossman, R. L. Ehman, *Fluoroscopically Triggered Contrast-Enhanced Three-dimensional MR Angiography with Elliptical Centric View Order: Application to the Renal Arteries"*, Radiology 1997, 205:137–146.

The in vivo contrast enhancement profile provided by the passage of a contrast agent bolus closely matches a gamma-variate function as described by the general equation:

$$C(t) = A t e^{-\frac{t}{\alpha}}.$$

As shown in FIG. 4, as a result of the contrast agent passage the acquired NMR signal is enhanced considerably for a short time interval and then the enhancement tapers off. Consequently, even if the MR acquisition is accurately synchronized to the contrast bolus, only a small number of views (usually the central k-space views) are acquired while the T1 shortening associated with high contrast agent concentration is at its peak. The bulk of the image is acquired while contrast concentration is decreasing and T1 time is increasing.

The predominant method for acquiring MRA data is to detect the arrival of the contrast bolus in the region of interest and trigger a centric view order image acquisition. As described, for example, in U.S. Pat. No. 5,122,747 the views are arranged in an order which samples the central region of k-space first and the most peripheral regions last. As shown in FIG. 4, if the contrast bolus arrives very quickly in the region of interest as indicated by curve 10, the leading edge of the contrast profile is very steep and the central k-space views acquired at the beginning of the triggered scan are synchronized very well with the peak contrast enhancement. High quality arterial phase MRA images are routinely obtained in this situation. On the other hand, when the bolus has a longer arrival time the leading edge of the contrast profile is not as steep as indicated by curve 12, and the initial views acquired after detection of bolus arrival will occur before peak contrast enhancement occurs. If a centric view order is employed in this latter situation, slight, but noticeable and undesirable edge enhancement occurs in the reconstructed image because some peripheral k-space views are acquired with greater contrast enhancement than some of the central k-space views.

One solution to this problem is to delay the centric view order scan several seconds after the arrival of the contrast bolus is detected. While this ensures that the central k-space views are acquired at peak contrast, it wastes a significant amount of time before the scan is triggered during which the contrast is relatively high. As a result, some of the peripheral views acquired at the end of the scan have much reduced contrast enhancement and image SNR is adversely affected.

SUMMARY OF THE INVENTION

The present invention is a method for acquiring MRA data during a contrast enhanced dynamic study in which the sampling of the center of k-space is synchronized with the peak in contrast agent enhancement. More specifically, the present invention is a method for acquiring MRA data in which a contrast agent is injected, the arrival of the contrast bolus in the region of interest is detected and a series of NMR imaging pulse sequences are performed in which k-space is sampled in an inward spiral pattern for a first time period during which contrast enhancement produced by the contrast bolus is increasing and k-space is sampled in an outward spiral pattern for a second time period during which contrast enhancement is decreasing.

A general object of the invention is to synchronize the acquisition such that the center of k-space is acquired at peak contrast enhancement. By sampling k-space in an inward spiral followed by an outward spiral, sampling of the center of k-space is precisely aligned, or synchronized, with the peak contrast enhancement.

Another object of the invention is to use the contrast enhancement provided by the passage of the contrast bolus to the maximum extent possible. The contrast enhancement provided by the leading edge of the contrast enhancement profile is utilized to acquire MRA data during the first time period. The contrast enhancement during this portion of the acquisition is much higher than the contrast enhancement provided near the end of a conventional centric view ordered scan.

Yet another object of the invention is to provide the above objectives without producing image artifacts. By interleaving the k-space location of samples acquired during the first time period with the k-space location of samples acquired during the second time period, samples acquired at the same k-space radius have substantially the same amount of contrast enhancement. This avoids over-enhancement of edges in the reconstructed image.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIG. 5 is a flow chart of a first preferred embodiment of a method according to the present invention;

GENERAL DESCRIPTION OF THE INVENTION

An objective of the invention is to initiate acquisition immediately upon detection of significant contrast enhancement in the vasculature of interest. However, the starting sampling point in k-space is not at the smallest possible radius, as in centric view ordering, but is at some nonzero radius. As data acquisition proceeds the k-space trajectory then moves radially inward (i.e. samples are progressively sampled at smaller k-space radii) in a spiral pattern. This is opposite the direction of increased radial k-space sampling of the conventional centric view order. This inward moving sample pattern occurs in synchrony with the rising contrast concentration in the vessels of interest, which occurs during the arrival of the contrast bolus. This inward moving sample trajectory is timed and sampled in such a way that at the peak in contrast enhancement the central-most views of k-space are sampled. Next, the acquisition proceeds using a centric view order in which k-space sampling moves radially outward. However, those k-space points which have been previously sampled on the inward trajectory are not sampled on the outward trajectory.

Successful implementation of this invention requires determination of the proper starting k-space radius as well as the spacing between samples during the radially inward trajectory. In general these are dependent on the shape of the specific contrast enhancement profile, a curve which typically is different from patient to patient. The optimal acquisition is one in which samples made on the rising and trailing edges of the contrast enhancement profile for the same value of enhancement are acquired at the same k-space radius.

Figure 4:
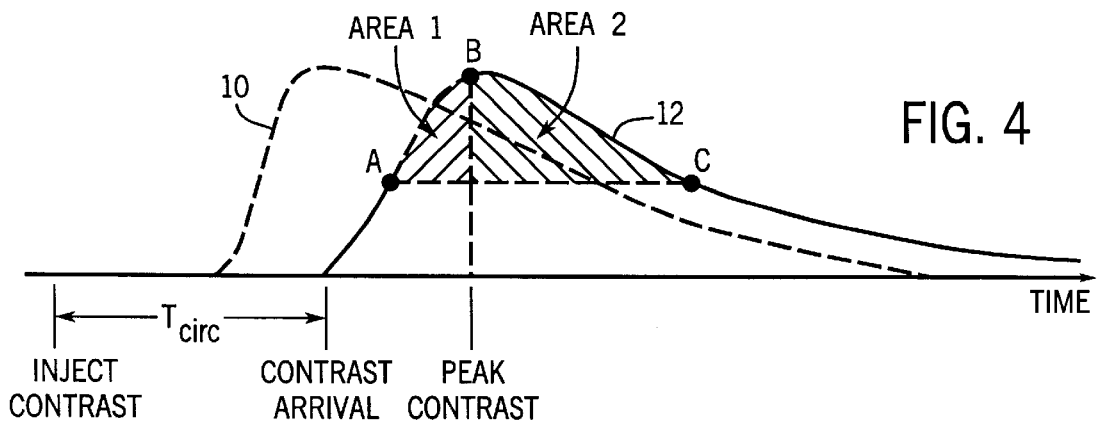
FIG. 4 is a graphic representation of typical contrast agent enhancement profiles.

Referring to FIG. 4, points A and C correspond to the same amount of contrast enhancement. Hence, data sampled at these points should be at the same k-space radius. The starting k-space radius is thus that which would also be sampled at the same relative contrast enhancement value on the trailing edge of the contrast enhancement profile. This starting point can be determined from knowledge of the total area under the contrast enhancement profile between points A and C and the repetition time (TR) of the imaging pulse sequence. The rate of k-space sampling for the inward spiral portion of the sampling is determined by comparing the relative areas under the contrast enhancement profile before and after peak contrast point B. In fact the sampling rates for the inward and outward portions of the sampling are proportional to these areas. That is, let Area1 be the area under the bolus curve between points A and B in FIG. 4 and let Area2 be the area under the curve between points B and C. Then the relative sampling rates in the inward and outward going portions of the spiral, called $S_{in}$ and $S_{out}$ respectively, are given by:

$$S_{in}/S_{out} = \text{Area1/Area2} \tag{1}$$

Further, the radius in the ky-kz plane at which to start the inward spiral can also be determined. This is found by determining the total number of k-space samples to be measured in the time interval between points A and C. If this time is T and the repetition time of the pulse sequence used is TR, then the total number of points sampled in this time is $$N = T/TR. \tag{2}$$

The first point sampled on the inward spiral would then be approximately the Nth point along the total desired spiral sampling trajectory where N is given by Eq. 2. In the limit where the leading edge of the contrast concentration curve profile is very steep, and the area under the profile before its peak B is infinitesimally small or zero, the relative sampling rate of the inward spiral approaches zero, and the view order reverts to a conventional centric order.

Figure 8:
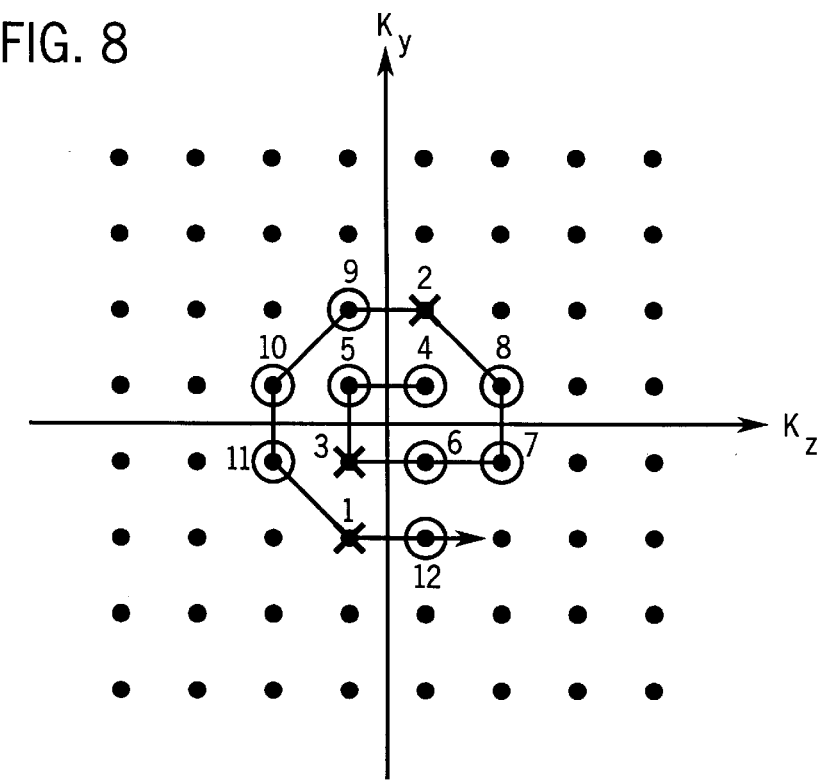
FIG. 8 is a graphic representation of an exemplary k-space sampling order according to the present invention.

A sample implementation is shown in FIG. 8. The specific points to be sampled match those for the conventional spiral centric case. If the ratio of areas before and after peak contrast is 1:3, then one point in k-space is sampled on the inward spiral portion for every three points on the outward spiral portion of the acquisition. This sampling ratio is referred to herein as the "interleave sample rate". Equivalently, on the inward spiral every fourth sample point is sampled. Referring to FIG. 8, the first point sampled corresponds to time point A of FIG. 4, and is identified with a "1". The next point is identified as a "2" and occurs four sample points inward along the spiral trajectory. The third sample point is shown as "3" and occurs another four sample points further inward. By this time the contrast is peak value, corresponding to time point B in FIG. 4, and point "4" is sampled in k-space. At this timepoint in the process an outward spiral centric view order begins, and points "5", "6", "7", etc. are sampled.

Implementation of this view order is more involved than a centric view order. By way of comparison, the conventional centric view order is dependent only on pre-determined technical parameters, namely the field of view and the desired spatial resolution. The calculated view order is loaded into the pulse sequence controller prior to contrast injection and is triggered upon detection of contrast arrival. The view order of the present invention is dependent upon patient-specific characteristics and particularly, the shape of the contrast enhancement profile. It is necessary either to measure or to estimate the rise time and the decay time of this profile prior to establishing the specific view order for a given patient.

Measurement of the contrast enhancement profile can be done with a small test bolus of contrast material. This procedure is already done at many clinical sites as a means of establishing the circulation time for determination of scan synchronization. The same test bolus can be used to measure arrival and decay time. This is not ideal because it causes contrast to be present prior to the actual diagnostic procedure itself.

An alternative method is to estimate the arrival and decay time parameters. This is done from knowledge of the general shape of the contrast enhancement profile and knowledge that the arrival time and decay time are related to bolus circulation time, $T_{CIRC}$ in FIG. 4. Typically, the longer the circulation time the longer are both of these parameters. This has been observed in experimental measurements of bolus profiles in patients. The bidirectional view order is then created on the fly during the dynamic study. The injection of contrast initiates a counter which measures elapsed time. At the outset a centric view order is loaded in the pulse sequence ready for execution when contrast arrival is detected. As the elapsed time increases, the view order is adjusted with the number of views acquired during the inward spiral portion of the sampling increasing as the measured circulation time increases.

DESCRIPTION OF THE PREFERRED EMBODIMENT

Figure 1:
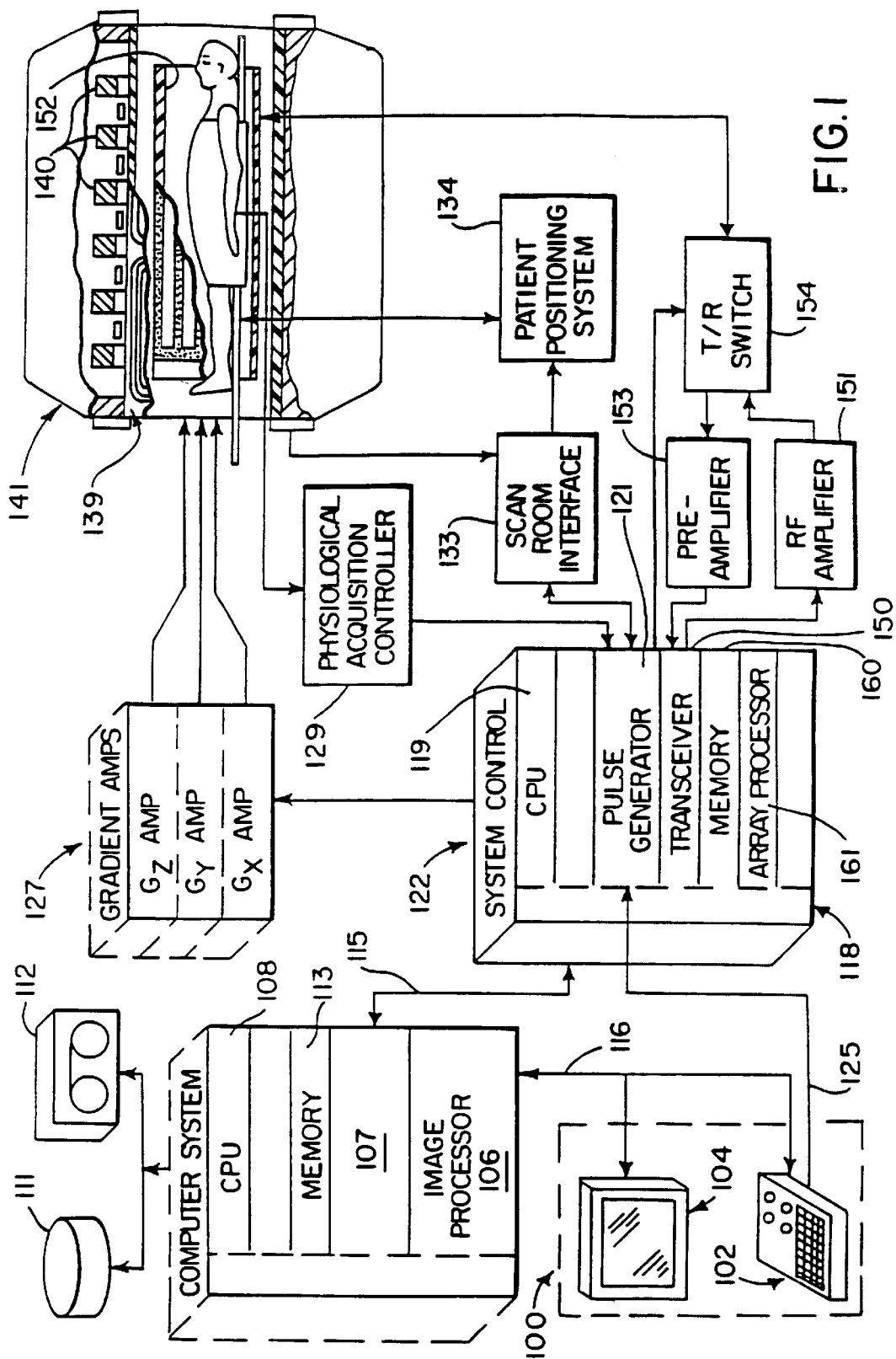
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane 118. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

Figure 2:
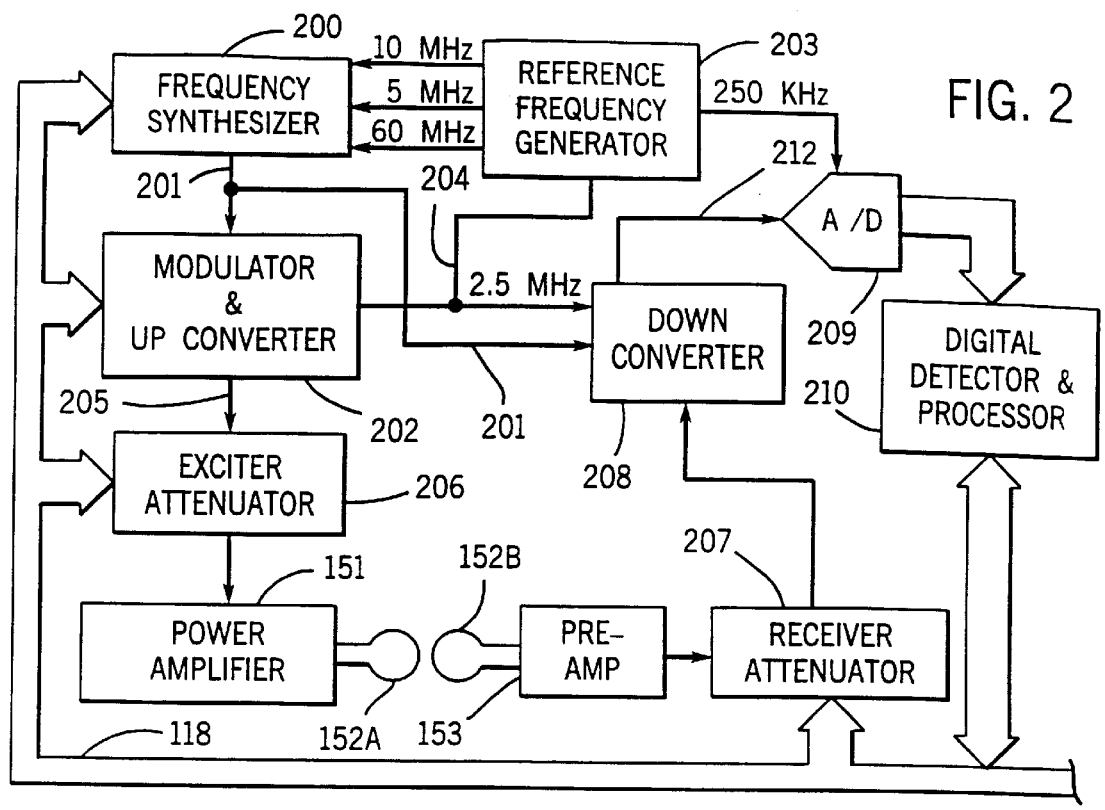
FIG. 2 is an electrical block diagram of the transceiver which forms part of the MRI system of FIG. 1.

Referring particularly to FIGS. 1 and 2, the transceiver 150 produces the RF excitation field B1 through power amplifier 151 at a coil 152A and receives the resulting signal induced in a coil 152B. As indicated above, the coils 152A and B may be separate as shown in FIG. 2, or they may be a single whole body coil as shown in FIG. 1. The base, or carrier, frequency of the RF excitation field is produced under control of a frequency synthesizer 200 which receives a set of digital signals from the CPU module 119 and pulse generator module 121. These digital signals indicate the frequency and phase of the RF carrier signal produced at an output 201. The commanded RF carrier is applied to a modulator and up converter 202 where its amplitude is modulated in response to a signal R(t) also received from the pulse generator module 121. The signal R(t) defines the envelope of the RF excitation pulse to be produced and is produced in the module 121 by sequentially reading out a series of stored digital values. These stored digital values may, in turn, be changed from the operator console 100 to enable any desired RF pulse envelope to be produced.

The magnitude of the RF excitation pulse produced at output 205 is attenuated by an exciter attenuator circuit 206 which receives a digital command, from the backplane 118. The attenuated RF excitation pulses are applied to the power amplifier 151 that drives the RF coil 152A. As will be described in more detail below, one aspect of the present invention is to modulate the flip angle produced by the RF excitation pulse during the scan by changing this digital command. For a more detailed description of this portion of the transceiver 122, reference is made to U.S. Pat. No. 4,952,877 which is incorporated herein by reference.

Referring still to FIGS. 1 and 2 the signal produced by the subject is picked up by the receiver coil 152B and applied through the preamplifier 153 to the input of a receiver attenuator 207. The receiver attenuator 207 further amplifies the signal by an amount determined by a digital attenuation signal received from the backplane 118.

The received signal is at or around the Larmor frequency, and this high frequency signal is down converted in a two step process by a down converter 208 which first mixes the NMR signal with the carrier signal on line 201 and then mixes the resulting difference signal with the 2.5 MHZ reference signal on line 204. The down converted NMR signal is applied to the input of an analog-to-digital (A/D) converter 209 which samples and digitizes the analog signal and applies it to a digital detector and signal processor 210 which produces 16-bit in-phase (I) values and 16-bit quadrature (Q) values corresponding to the received signal. The resulting stream of digitized I and Q values of the received signal are output through backplane 118 to the memory module 160 where they are employed to reconstruct an image.

The 2.5 MHZ reference signal as well as the 250 KHz sampling signal and the 5, 10 and 60 MHZ reference signals are produced by a reference frequency generator 203 from a common 20 MHZ master clock signal. For a more detailed description of the receiver, reference is made to U.S. Pat. No. 4,992,736 which is incorporated herein by reference.

Figure 3:
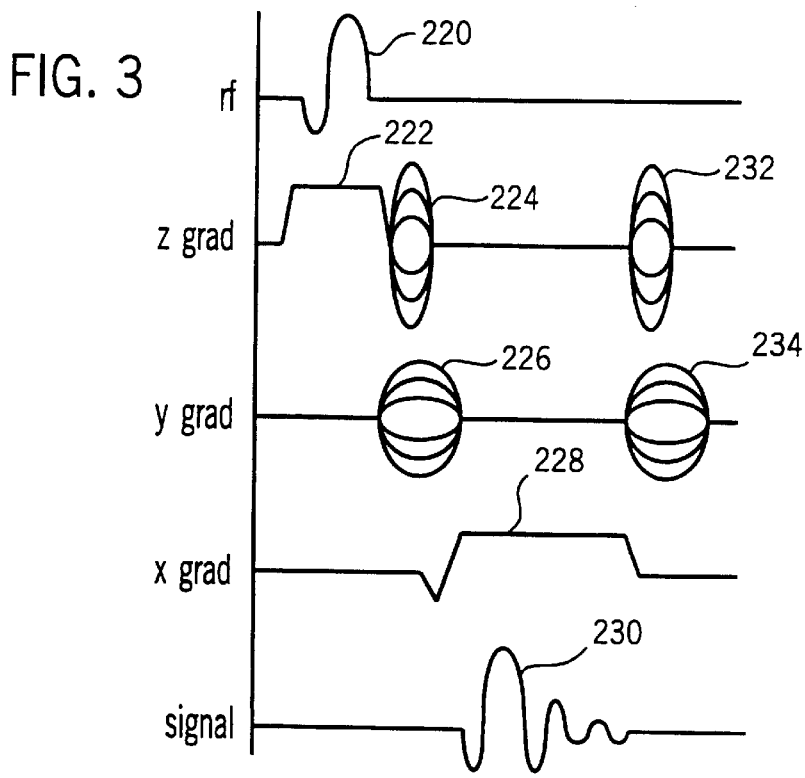
FIG. 3 is a graphic representation of the imaging pulse sequence employed in the preferred embodiment of the invention.

Although the present invention can be used with a number of different pulse sequences, the preferred embodiment of the invention employs a 3D gradient recalled echo pulse sequence depicted in FIG. 3. The pulse sequence "3dfgre" available on the General Electric 1.5 Tesla MR scanner sold under the trademark "SIGNA" with revision level 5.5 system software was used.

Referring particularly to FIG. 3, an RF excitation pulse 220 is produced in the presence of a slab select gradient pulse 222 to produce transverse magnetization in the 3D volume of interest as taught in U.S. Pat. No. 4,431,968. This is followed by a phase encoding gradient pulse 224 directed along the z axis and a phase encoding gradient pulse 226 directed along the y axis. A readout gradient pulse 228 directed along the x axis follows and a partial echo (60%) NMR signal 230 is acquired and digitized as described above. After the acquisition, rewinder gradient pulses 232 and 234 rephase the magnetization before the pulse sequence is repeated as taught in U.S. Pat. No. 4,665,365.

As is well known in the art, the pulse sequence is repeated and the phase encoding pulses 224 and 226 are stepped through a series of values to sample the 3D k-space. In the preferred embodiment 32 phase encodings are employed along the z axis and 192 phase encodings are employed along the y axis. For each particular y phase encoding, therefore, 32 acquisitions with 32 different z phase encodings are performed to sample completely along the $k_z$ axis. This is repeated 192 times with 192 different y phase encodings to sample completely along the $k_y$ axis.

Sampling along the $k_x$ axis is performed by sampling the echo signal 230 in the presence of the readout gradient pulse 228 during each pulse sequence. It will be understood by those skilled in the art that only a partial sampling along the $k_x$ axis is performed and the missing data is computed using a homodyne reconstruction or by zero filling. This enables the echo time (TE) of the pulse sequence to be shortened to less than 1.8 to 2.0 ms. and the pulse repetition rate (TR) to be shortened to less than 10.0 msecs.

For assessing overall blood vessel structure and health it is sometimes useful to project the 3D array of image data into a single 2D projection image. The most commonly used technique for doing this is to project a ray from each pixel in the 2D projection image through the 3D array of image data points and select the data point which has the maximum value. The value selected for each ray is used to control the brightness of its corresponding pixel in the 2D projection image. This method, referred to as the "maximum pixel technique," is very easy to implement and it gives aesthetically pleasing images.

As indicated above the views used to form the 3D k-space data set are acquired over a period of time during which contrast agent is flowing into the region of interest ("ROI"). As a result, the amount of contrast agent, and hence the effective $T_1$ of the blood flowing through the ROI will change during the acquisition of the views used to form the image data set. As a result, signal enhancement occurs during the image acquisition and the amount of enhancement depends on the contrast enhancement profile produced by the contrast bolus passage.

Figure 6:
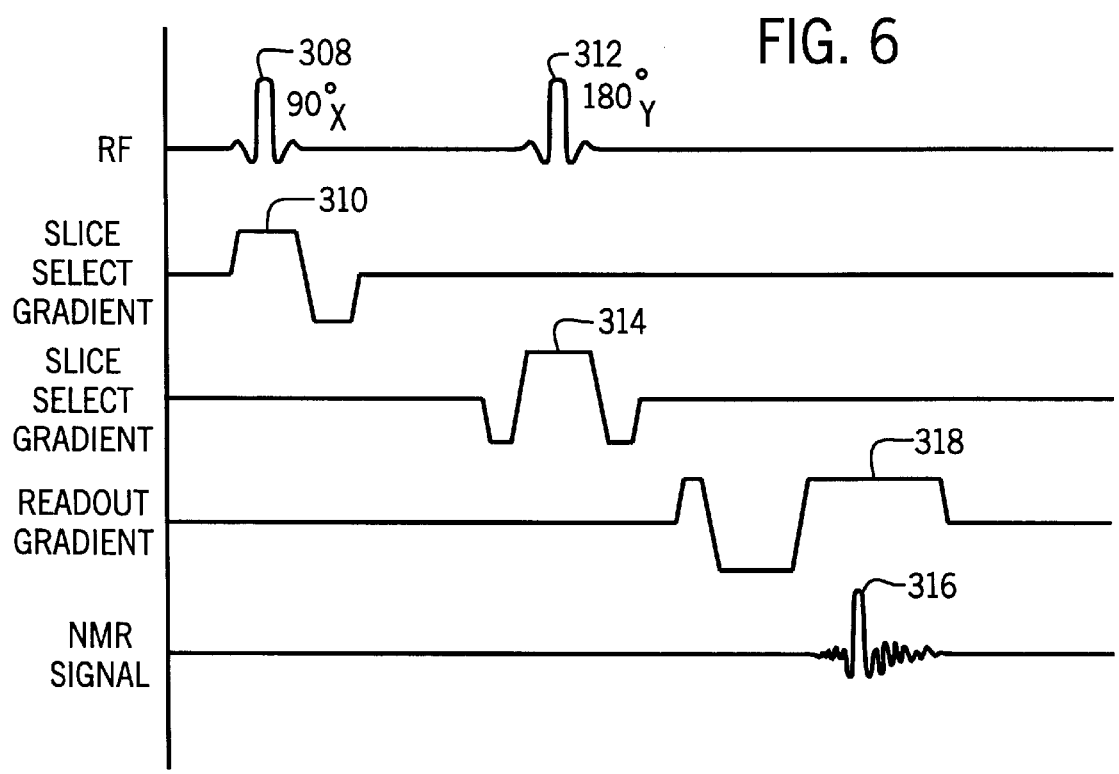
FIG. 6 is a graphic representation of a contrast concentration measurement pulse sequence used in the method of FIG. 5.

The first preferred technique for practicing the present invention calculates the view order to be used during the image acquisition based on the arrival time of the contrast bolus in the region of interest. Referring particularly to FIG. 5, with this embodiment of the invention the pulse sequence prescription is entered into the MRI system as indicated at process block 300 and the patient is injected with a contrast agent as indicated at process block 302. When this occurs a timer is started as indicated by process block 303 and a loop is entered in which the contrast concentration pulse sequence of FIG. 6 is performed by the MRI system to acquire contrast data as indicated at process block. The contrast data is compared with a threshold value at decision block 306 to determine if the contrast bolus has arrived.

Referring to FIG. 6, the contrast concentration pulse sequence is commercially available on the General Electric MRI system as part of the Smart Prep feature. It includes a 90° rf excitation pulse 308 which is applied in the presence of a slice select gradient pulse 310, followed by a 180° rf refocusing pulse 312 applied in the presence of a second slice select gradient pulse 314. The first and second slice select gradient 310 and 314 are directed along orthogonal axes (e.g. z and y axes) and they intersect in the ROI. An NMR signal 316 is acquired in the presence of a readout gradient pulse 318, and the acquired NMR signal is integrated and stored as a concentration value.

The use of the pulse sequence in FIG. 6 as described above provides an automatic method for determining bolus arrival in the region of interest. An alternative method for accomplishing this task is preferred when the attending physician is to determine bolus arrival. With this embodiment a fluoroscopic image is produced using a 2D gradient echo sequence with TR and TE times of 9 and 2.4 msec. respectively. A spatial resolution of 256 (x-axis) by 128 (y-axis) is used and first order gradient moment nulling is employed along the slice select and readout axes. A partial echo readout is used in which 160 points are sampled (32 at negative and 128 at positive kx values) using a signal bandwidth of ±16 kHz. All fluoroscopic images are reconstructed using a system such as that described in U.S. Pat. No. 4,830,012 which is interfaced to the MRI system. Reconstruction time for each 256×256 displayed image from data acquired with a single coil is approximately 300 msec. and for data from a four-channel multi-coil is approximately 600 msec. Partial image updating is used so that images are reconstructed at rates imposed by reconstruction times, and not the intrinsic temporal resolution (TR×128 phase encodes) of the pulse sequence. The central k-space views are sampled more frequently than the higher spatial frequency views, resulting in fluoroscopic image sequence rates of 3.5 images/sec. This enables the physician to monitor the region of interest and observe precisely when the contrast bolus arrives.

Referring again to FIG. 5, when the arrival of the contrast bolus is detected the timer is stopped as indicated at process block 308. The timer indicates $T_{CIRC}$ which is used in subsequent calculations indicated at process block 310 to determine the optimal view order of the image acquisition. These calculations are based on the presumption that the delay time $T_{CIRC}$ is determinant of the shape of the contrast enhancement profile. Based on this shape, the number of k-space samples to be acquired during the inward spiral portion of the sampling view order is determined from a look-up table as well as the interleave ratio.

After the optimal view order is determined, the image data is acquired using the pulse sequence of FIG. 3 as indicated by process block 312. An image is reconstructed from the acquired image data as indicated by process block 314 and described above.

Figure 7:
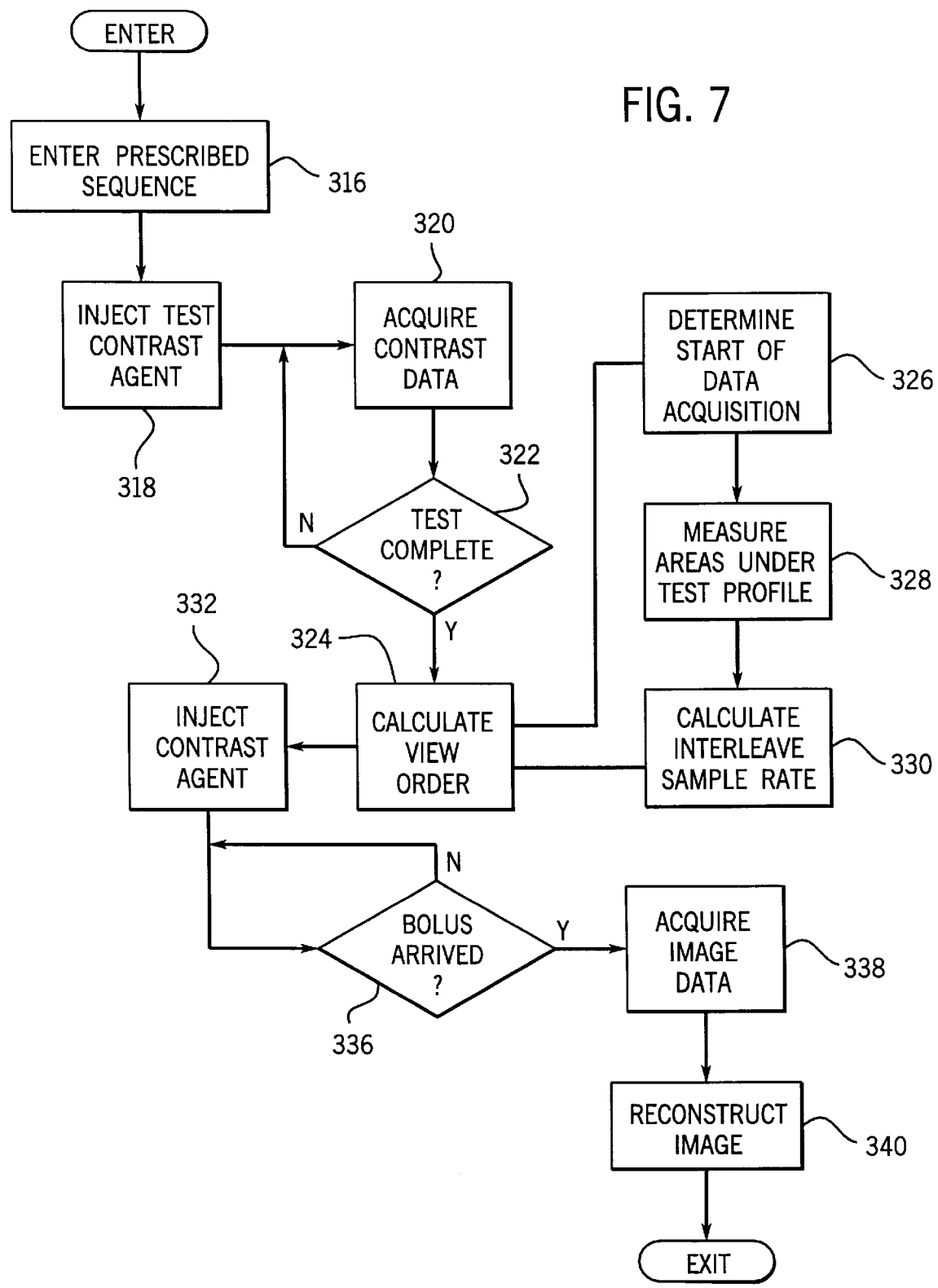
FIG. 7 is a flow chart of a second preferred embodiment of a method according to the present invention.

The alternative embodiment of the invention performs a prescan with a test bolus of contrast agent to actually measure the contrast enhancement profile in the region of interest. Referring particularly to FIG. 7, the prescribed pulse sequence parameters are entered into the MRI system as indicated at process block 316 and a test bolus of contrast agent is injected into the patient as indicated at process block 318. The contrast concentration pulse sequence of FIG. 6 is performed to acquire contrast data, as indicated at process block 320, and this acquisition is repeated until the contrast bolus has passed through the region of interest as determined at decision block 322. The acquired contrast data is stored as a function of time to form a contrast enhancement profile such as that indicated by curve 10 or curve 12 in FIG. 4.

As indicated at process block 324, the view order for the image acquisition is determined from the stored test bolus contrast enhancement profile. As indicated by process block 326, this includes determining the time interval after contrast bolus arrival at which image acquisition will begin. This corresponds to point A in FIG. 4. The peak of the contrast enhancement profile (point B) and point C on the trailing edge of the profile are located and the areas under the profile between points A and B and between B and C are calculated as indicated at process block 328. The prescribed pulse repetition rate, TR, of the imaging pulse sequence determines the number of views that can be acquired during the time interval between points A and B. These will be acquired along an inward spiral sampling trajectory as described above. The interleave sample rate of this first portion of the image acquisition is determined at process block 330 by the relative values of the measured areas as described above. From this information a view order table is produced and stored in the pulse generator 121 (FIG. 1).

The prescribed scan then begins by injecting the patient with a full dose of contrast agent as indicated at process block 332. When the contrast bolus arrives in the region of interest as determined by the previously measured bolus arrival time at block 336, the image data acquisition is started at process block 338. This acquisition is performed using the stored view order table, and when all views have been acquired, a 3D image is reconstructed as indicated at process block 340.

What is claimed is:

1. A method for acquiring MRA data with an MRI system, the steps comprising:
   a) injecting the patient with a contrast agent that enhances NMR signals;
   b) detecting arrival of contrast agent in a region of interest to be imaged;
   c) performing a series of imaging pulse sequences with the MRI system after detecting the arrival of contrast agent in step b) to acquire MRA data from the patient from which an image of the region of interest can be reconstructed, this acquisition including:
      i) a first acquisition time period prior to peak NMR signal enhancement by the contrast agent during which a portion of said series of imaging pulse sequences are performed to sample k-space in a trajectory directed inward toward the center of k-space; and
      ii) a second acquisition time period after peak enhancement by the contrast agent during which the remainder of said series of imaging pulse sequences are performed to sample k-space in a trajectory directed outward away from the center of k-space.

2. The method as recited in claim 1 in which k-space sampling is acquired from a single spiral pattern and samples acquired during the first acquisition time period are interleaved in this spiral pattern with samples acquired during the second acquisition time period.

3. The method as recited in claim 2 in which the interleave sample rate during the first acquisition time period is determined from the shape of a contrast enhancement profile produced by contrast agent.

4. The method as recited in claim 3 in which the contrast enhancement profile is produced by:

injecting the patient with a test dose of the contrast agent prior to performing step a); and performing a series of pulse sequences with the MRI system to measure the NMR signal enhancement in the region of interest as the test contrast agent flows therethrough.

5. The method as recited in claim 3 in which the interleave sample rate is determined by calculating a first area beneath the contrast enhancement profile prior to peak enhancement and second area beneath the contrast enhancement profile after the peak enhancement.

6. The method as recited in claim 5 in which the interleave sample rate is proportional to the ratio of the first and second areas.

7. The method as recited in claim 1 which includes:

d) timing the interval ($T_{CIRC}$) between injecting the patient with contrast agent in step a) and detecting the arrival of the contrast agent in the region of interest in step b); and e) determining the length of the first acquisition time period using the interval ($T_{CIRC}$).

8. The method as recited in claim 7 in which k-space sampling is acquired from a single spiral pattern and samples acquired during the first acquisition time period are interleaved in this spiral pattern with samples acquired during the second acquisition time period.

* * * * *

UNITED STATES PATENT AND TRADEMARK OFFICE
CERTIFICATE OF CORRECTION

PATENT NO. : 6,201,986 B1
DATED : March 13, 2001
INVENTOR(S) : Riederer et al.

It is certified that error appears in the above-identified patent and that said Letters Patent is hereby corrected as shown below:

Column 1,
Directly above "BACKGROUND OF THE INVENTION", please insert the following: under a separate heading of "Government License Rights"
"The U.S. Government has a paid-up license in this invention and the right in limited circumstances to require the patent owner to license others on reasonable terms as provided for by the terms of CA37993 awarded by the National Institutes of Health."

Signed and Sealed this

Eleventh Day of December, 2001

*Attest:*

NICHOLAS P. GODICI
*Attesting Officer*    *Acting Director of the United States Patent and Trademark Office*